United States Patent [19]
White

[11] Patent Number: 5,243,516
[45] Date of Patent: Sep. 7, 1993

[54] BIOSENSING INSTRUMENT AND METHOD

[75] Inventor: Bradley E. White, Zionsville, Ind.

[73] Assignee: Boehringer Mannheim Corporation, Indianapolis, Ind.

[21] Appl. No.: 451,309

[22] Filed: Dec. 15, 1989

[51] Int. Cl.$^5$ .................... G06F 15/42; G01N 27/26
[52] U.S. Cl. ............................... 364/413.07; 204/401
[58] Field of Search ............... 364/413.07, 413.11; 204/401, 403, 406; 435/817

[56] References Cited

U.S. PATENT DOCUMENTS 4,340,458 7/1982 Lerner et al. .................... 128/635 X

FOREIGN PATENT DOCUMENTS

| | | |
|---|---|---|
| 0230472 | 8/1987 | European Pat. Off. . |
| 0044593 | 4/1979 | Japan ................................. 204/401 |
| WO89/08713 | 9/1989 | PCT Int'l Appl. . |

Primary Examiner—Roy N. Envall, Jr.
Assistant Examiner—David Huntley
Attorney, Agent, or Firm—Perman & Green

[57] ABSTRACT

A biosensing system is described which determines whether a measured current is varying in accordance with a predetermined Cottrell current relationship. The system includes a test cell with at least a pair of electrodes which extend into a reaction zone, which reaction zone includes analyte reactants. An analog signal detector, in combination with a microprocessor, take plurality of current measurements between the electrodes over a plurality of succeeding measurement times, after a sample is placed in contact with the analyte reactants in the reaction zone. The microprocessor also stores a plurality of succeeding cpmparison constants which are derived by taking the inverse ratio of the square root of a measurement time divided by the square root of a subsequent measurement time. The microprocessor selects a pair of succeeding measurement times; derives a ratio of the currents measured at those times; and then compares the ratio of those currents with the comparison constant previously derived for the pair of succeeding measurement times. If the comparison indicates that the measured current ratio is dissimilar from the comparison constant, an indication is developed that the current between the electrodes is not varying in accordance with the Cottrell relationship. The plurality of current measurements are also used to calculate total charge transferred, Q. Q can then be used as a second means of calculating the final result.

8 Claims, 4 Drawing Sheets

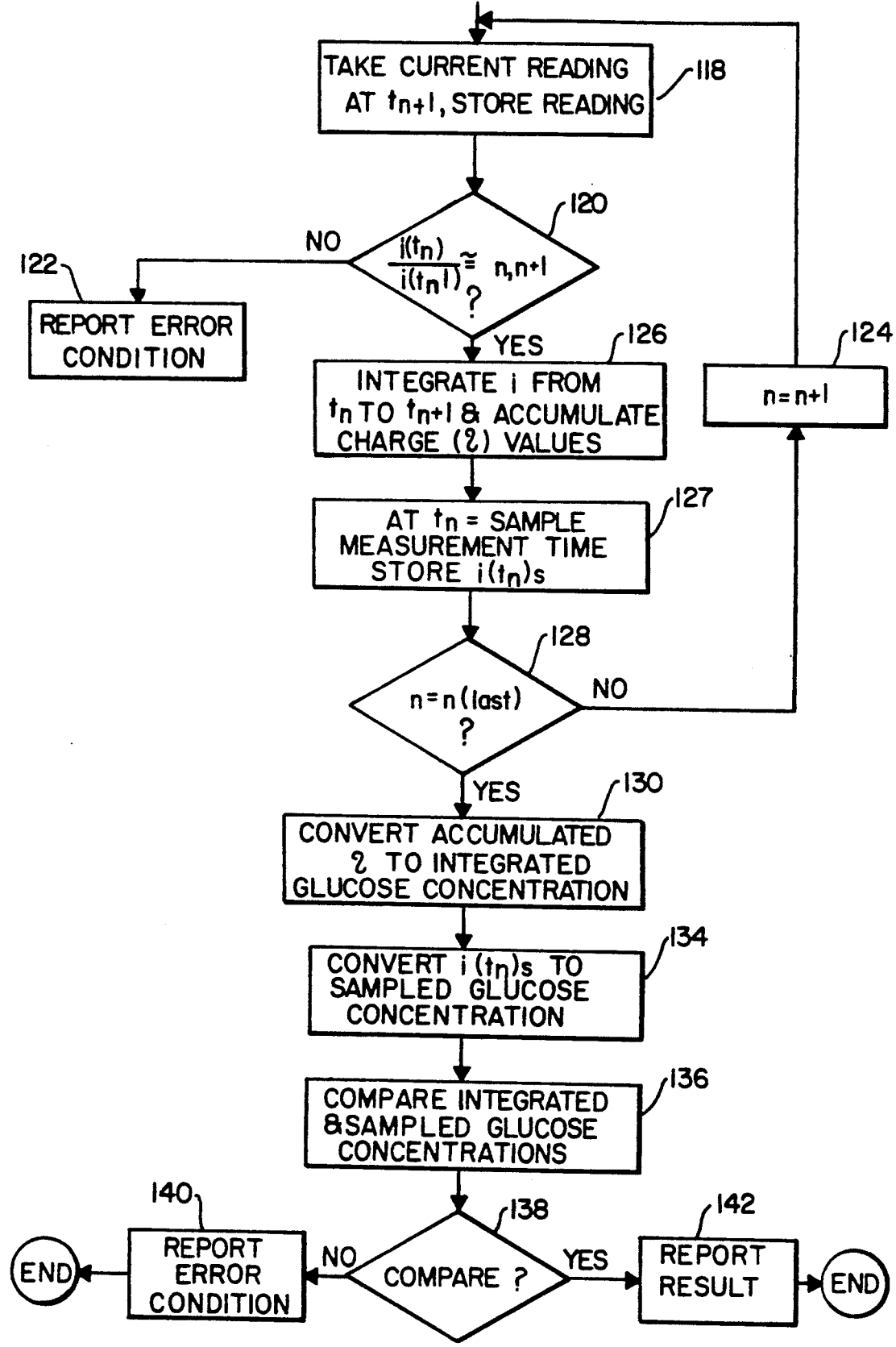

BIOSENSING INSTRUMENT AND METHOD

FIELD OF THE INVENTION

This invention relates to a biosensing instrument for quantitatively determining the concentration of an analyte in a fluid sample, and more particularly, to a method and apparatus for amperometrically determining the concentration of biological compounds, such as glucose, cholesterol, etc., in a body fluid such as blood.

REFERENCE TO RELATED APPLICATIONS

This invention is related to inventions described in:
U.S. patent application Ser. No. 07/451,107, filed Dec. 15, 1989, now U.S. Pat. No. 4,963,814, entitled "Regulated Bifurcated Power Supply" by Parks and White.

U.S. patent application Ser. No. 07/451,212, filed Dec. 15, 1989, now U.S. Pat. No. 4,999,632, entitled "Analog to Digital Conversion With Noise Reduction" by Parks.

U.S. patent application Ser. No. 07/451,108, filed Dec. 15, 1989, now U.S. Pat. No. 4,999,582, entitled "Biosensor Electrode Excitation Circuit" by Parks and White.

BACKGROUND OF THE INVENTION

Recently, biosensors employing enzymes have been applied to the detection of both glucose and cholesterol concentrations in blood samples. In European Patent Application 0 230 472 to Nankai et al., a biosensing instrument is disclosed which employs amperometric measurements to determine glucose concentration in a blood sample. The instrument employs a test cell with measuring, reference and counter electrodes. Overlaying the electrodes is an insert which contains glucose oxidase, potassium ferricyanide and other components. When a blood sample is placed in contact with the insert, glucose in the sample reacts with the potassium ferricyanide (through the action of the glucose oxidase) to form potassium ferrocyanide. A subsequent application of a voltage to the electrodes induces a reversal of the reaction and a current flow which is proportional to the concentration of the potassium ferrocyanide formed in the initial reaction. A measure of the current flow is said to correspond to the concentration of glucose in the sample.

A similar system for measuring both glucose and cholesterol concentrations is disclosed in PCT International Application No. WO 89/08713 of Pottgen et al. Both the Nankai et al. and the Pottgen et al. systems employ similar chemistries to enable amperometric detection of glucose concentrations. For glucose, both rely upon the catalytic action of glucose oxidase on glucose to enable the conversion of potassium ferricyanide (+3) to potassium ferrocyanide (+4), (i.e., the "forward" reaction). A subsequent application of a potential across the reactants electrochemically causes a reversal of the reaction, (i.e. the "reverse" reaction). Upon the oxidation of glucose by glucose oxidase, electrons are transferred to ferricyanide causing its reduction yielding ferrocyanide. An applied potential to the electrode electrochemically oxidizes ferrocyanide back to ferricyanide with the electrons transferred to the electrode. This creates a small and detectable electrical current whose level is proportional to the level of glucose concentration in the sample. The current which results during the reverse reaction is known as the Cottrell current and is described by the following equation:

$$\text{Cottrell Current} = i = \frac{nF\sqrt{D}\ CA}{\sqrt{\pi} \cdot \sqrt{t}} \quad (1)$$

where:
n = the number of transferred electrons;
F = Faraday's constant
A = area of measuring electrode;
C = concentration of the analyte;
D = diffusion coefficient of the electroactive species;
t = time Equation 1 can be reduced to a simpler expression by realizing that most of the factors in the equation are constants for any particular test system. Thus, the Cottrell current, at any particular time during the reverse reaction, is shown by the following:

$$i_t = K \cdot \frac{C}{\sqrt{t}} \quad (2)$$

$$\text{where } K = \frac{nF\sqrt{D}\ A}{\sqrt{\pi}}$$

Equation 2 indicates that the Cottrell current is proportional to the concentration of the analyte and is inversely proportional to the square root of the measurement time. Plots of Cottrell current variations at various glucose concentration levels, are shown by the curves in the right upper quadrant of FIG. 3.

The prior art has characteristically selected a particular time during the reverse reaction to obtain a reading of the Cottrell current and converted that reading into a measure of glucose or cholesterol concentration. Neither Nankai et al. or Pottgen et al. deal with certain real-life problems which occur during the use of a test cell. For instance, if the blood sample does not totally cover the sensing electrode surfaces, an erroneous reading results. Furthermore, if the reaction area becomes hydrated, either prior to or during the test, an erroneous reading occurs. Likewise, if there is leakage along the length of the electrodes so that the blood sample covers not only the portion of the electrodes in the reaction zone, but also outside of the reaction zone, again, erroneous readings will occur. These errors appear as baseline shifts in the Cottrell current or modulations of area during the measurement period.

Accordingly, it is an object of this invention to provide an amperometric biosensor and method which both provides analyte concentration readings and prevents erroneous readings from being reported as true.

It is another object of this invention to provide an amperometric biosensor and method for glucose concentration which provides an error indication, if an aberrant current curve results.

SUMMARY OF THE INVENTION

A biosensing system is described which determines whether a measured current is varying in accordance with a predetermined Cottrell current relationship. The system includes a test cell with at least a pair of electrodes which extend into a reaction zone, which reaction zone includes analyte reactants. An analog signal detector, in combination with a microprocessor, take plurality of current measurements between the electrodes over a plurality of succeeding measurement times, after a sample is placed in contact with the analyte reactants in the reaction zone. The microprocessor also stores a plurality of succeeding comparison constants which are derived by taking the inverse ratio of the square root of a measurement time divided by the square root of a subsequent measurement time. The microprocessor selects a pair of succeeding measurement times; derives a ratio of the currents measured at those times; and then compares the ratio of those currents with the comparison constant previously derived for the pair of succeeding measurement times. If the comparison indicates that the measured current ratio is dissimilar from the comparison constant, an indication is developed that the current between the electrodes is not varying in accordance with the Cottrell relationship.

DESCRIPTION OF THE DRAWINGS

FIGS. 5 and 6 illustrate a high level flow diagram of the measurement process utilized by the system of FIG. 4.

DETAILED DESCRIPTION OF THE INVENTION

Figure 1:
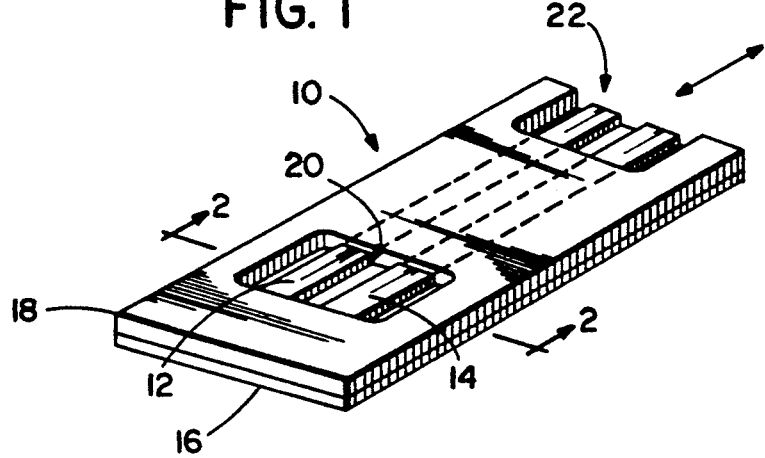
FIG. 1 is a perspective view of a test cell used with the biosensing instrument.

Referring now to FIG. 1, a pluggable test cell 10 includes a pair of electrodes 12 and 14. Electrode 12 is termed the "working" electrode and is preferably comprised of platinum, palladium, or other noble metal. Electrode 14 is a reference electrode and is preferably comprised of silver/silver oxide or silver/silver chloride. Electrodes 12 and 14 are sandwiched between a pair of polymeric sheet materials 16 and 18 with sheet material 18 having openings 20 and 22 that expose the electrodes. Opening 20 creates, in effect, a reaction zone or "well" wherein a sample of body fluid can be emplaced to enable a reaction to occur. Opening 22 exposes electrodes 12 and 14 so that the test cell 10 may be plugged into a female connector that makes electrical connections to the electrodes.

Figure 2:
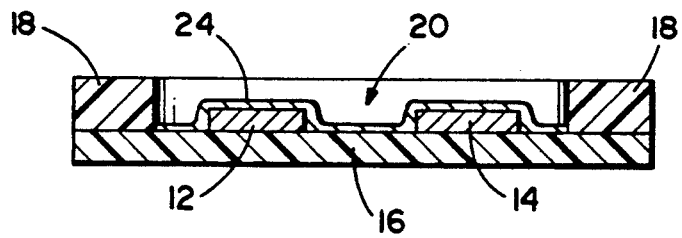
FIG. 2 is a section taken along line 2—2, in FIG. 1.

In FIG. 2, a section of test cell 10 is shown. During manufacture, a reaction layer 24 is emplaced in well 20 and provides the reactants for the biosensing reaction. If the instrument is to be used for glucose concentration determinations, layer 24 will include an enzyme, an electrolyte, a mediator, certain film formers, and a buffer. For instance, the enzyme may be glucose oxidase (or glucose dehydrogenase); the buffer may be organic or inorganic; the electrolyte may be potassium chloride or sodium chloride; the mediator is preferably potassium ferricyanide and the film formers comprise gelatin and propiofin. If the test cell is to be employed for cholesterol concentration determination, the enzyme would preferably be cholesterol oxidase with or without a cholesterol esterase additive. The buffer is preferably inorganic and includes an electrolyte such as potassium chloride or sodium chloride. In this case, two mediators are used, i.e. ferricyanide and quinones, and are placed in a gelatin film, as indicated above.

As stated in the introduction hereto, the chemistries employed by this system are known in the art and will not be described in significant detail. Suffice to say that glucose concentration is determined by initially emplacing in well 20, a sample of blood. The glucose within the sample causes a forward reaction of potassium ferricyanide conversion to potassium ferrocyanide. When the forward reaction has proceeded to completion, a subsequent application of a voltage across terminals 12 and 14 will see the creation of a small current therebetween that results from the reverse reaction of potassium ferrocyanide back to potassium ferricyanide. The flow of electrons during the reverse reaction is sensed and measured and has been found to bear a known relationship to glucose concentration levels.

Figure 3:
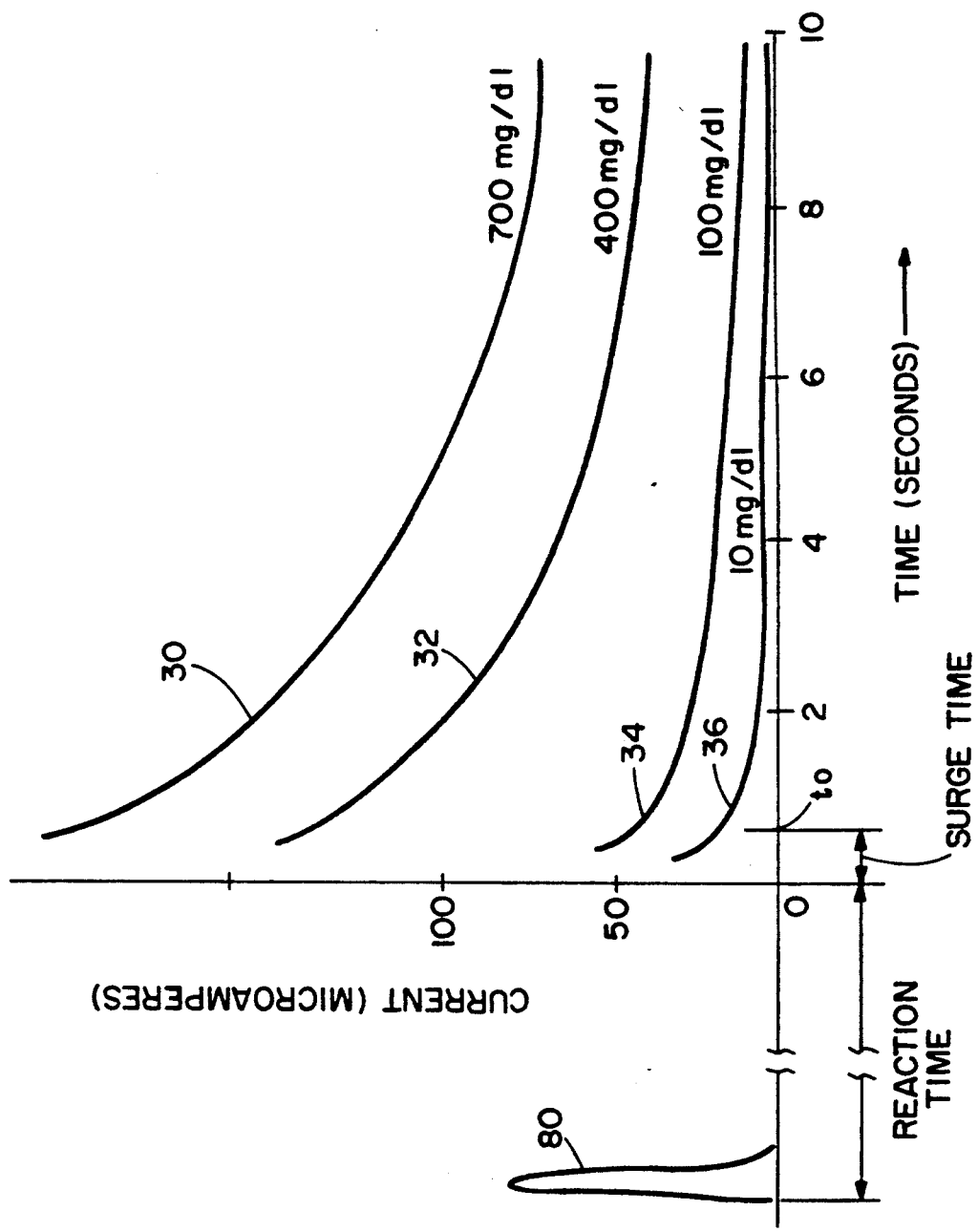
FIG. 3 is a chart showing variations of current over time which result when various concentrations of glucose are present in the test cell of FIG. 1.

In FIG. 3, a chart illustrates the current variations which occur with various levels of glucose concentration. Current in microamperes is plotted along the chart's vertical axis and time is plotted along its horizontal axis. Curves 30, 32, 34, and 36 illustrate the changes of current with the passage of time, after a potential is applied between electrodes 12 and 14 to initiate the reverse reaction. It can be seen that each of those curves follows a different path which is dependent upon the glucose concentration present in the blood sample.

As above described, the shape of each of the current curves 30, 32, 34, 36 etc. is described by equation 1. This, of course, assumes that the test conditions are as precisely defined and followed. Since the test cell of FIG. 1 and its allied measuring instrument (to be hereinafter to be described with respect to FIG. 4) are designed to be used by other than skilled technicians, it may often occur that the required test conditions are not met. For instance, it is critical that the blood sample be properly emplaced within well 20 for the glucose determination to be accurate. If the sample only covers a portion of the electrode areas, an erroneous reading will occur. If there is contamination in well 20 between electrodes 12 and 14, when a voltage is applied thereacross, the current curve which results may have no relationship whatsoever to glucose concentration. Furthermore, if there is a defect in the test cell which allows some of the blood sample to infiltrate between sheets 16 and 18 (e.g. along the sides of conductors 12 or 14), an erroneous reading will occur. The prior art test cells which have employed Cottrell current measurements have not taken these problems into account and have assumed, that with one measurement, the Cottrell current/time relationship is obtained.

While the above problem could be overcome by including a complex curve fitting algorithm into the microprocessor that controls the instrument, a much simpler and less complex technique for providing fail-safe measurement indications has been found. As can be seen from equation 2, the Cottrell current at any time is inversely proportional to the square root of the time at which the measurement is taken. Thus, Cottrell current measurements taken at two succeeding measurement times t1 and t2 can be expressed as:

$$i_{(t1)} = K \frac{C}{\sqrt{t1}} \qquad (3)$$

$$i_{(t2)} = K \frac{C}{\sqrt{t2}} \qquad (4)$$

The ratio of the measured Cottrell currents can be expressed as:

$$\frac{i_{(t1)}}{i_{(t2)}} = \frac{\sqrt{t2}}{\sqrt{t1}} = x_{1,2} \quad (5)$$

From equation 5, it can be seen that the ratio (e.g. $X_{1,2}$) of Cottrell currents measured at two succeeding times (e.g., t1, t2), is the same as the inverse of the ratio of the square roots of the times at which the measurements were taken. Thus the inverse ratio of the time square roots (designated as $x_{1,2}$ or "comparison ratio") is, for all glucose concentration curves, a constant.

Equation 5 shows that even though individual measurement currents taken at subsequent measurement times are not known in advance, that the ratio thereof, assuming a Cottrell curve is being followed, will be a constant and will show a level of similarity with the ratio of the square roots of the measurement times. Of course, the ratios will rarely be exactly alike as the current measurements will show some variations due to test conditions. As a result, any comparison of the ratios will require that standard deviations be taken into account when the comparison is made.

Figure 4:
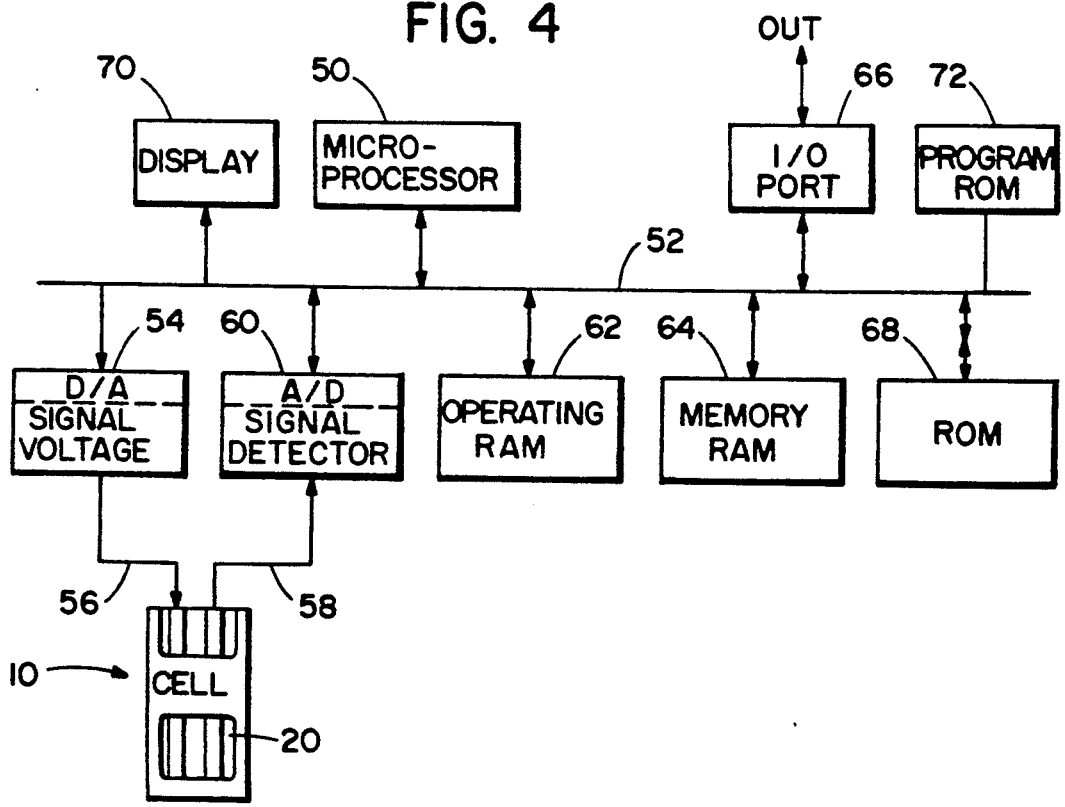
FIG. 4 is a block diagram of the test system used to determine the concentration of an analyte in a fluid sample.

Turning now to FIG. 4, a high level block diagram of the biosensing instrument is illustrated. Overall system control emanates from microprocessor 50 via system bus 52. System communications occur over system bus 52 and each of the operating units within the instrument interface therethrough. A signal voltage module 54 converts digital commands from microprocessor 50 into analog outputs which are then applied to cell 10 via line 56. (It should be remembered that cell 10, in an actual embodiment, is pluggable and only experiences stimulus voltages from signal voltage module 54 when it is inserted into a female plug.)

Current flow is returned through cell 10, via conductor 58, by signal detector 60 which, in turn, measures the current on a continuing basis and converts the readings to digital outputs. Signal detector 60 is controlled by a clock input from microprocessor 50 and, when a test voltage is applied to cell 10, it begins providing current readings on continuing basis. For instance, while the reverse reaction may take up 10 seconds to complete, signal detection module 60 will, during these 10 seconds, be taking current reading once every 500 milliseconds.

Random access memories (RAM's) 62 and 64 provide the operating memory for the instrument. RAM 62 provides storage for operating parameters. RAM 64 provides additional storage which enables previous measurement cycles to be retained for comparison purposes or for later read-out to another processor via input/output port 66. A pluggable read-only-memory (ROM) 68 interfaces with bus 52, and in addition to other data, H contains precalculated comparison constants ($x_{1,2}$, $X_{2,3}$ etc.) for the batch of test cells from which test cell 10 is taken. Program ROM 72 contains the software to operate the microprocessor. Likewise, it is known that a Cottrell current measurement taken at a single measurement time bears a linear relationship to glucose concentration. The linear relationship may, however, vary somewhat with different batches of cells. Therefore, ROM 68, can be supplied along with a batch of cells and will further include calibration constants to enable the linear relationship between Cottrell current and concentration, for the specific batch of cells, to be precisely defined for microprocessor 50. Finally, a display 70 enables the user to see the results of a concentration measurement taken through the use of cell 10.

The overall operation of a system can be understood by examining FIG. 3 in combination with FIG. 4. Initially, cell 10 is plugged into the instrument, and the user depresses a key (not shown) to indicate that the test is about to begin. Microprocessor 50 then causes signal voltage module 54 to apply an "autodrop" potential to the cell via line 56. Then, when a sample or "drop" of blood is placed in well 20, an immediate spike of current occurs, indicating the presence of the blood sample, and is sensed by a signal detector module 60. That current spike is indicated by curve 80 in FIG. 3. Upon sensing current spike 80, microprocessor 50 causes signal voltage module 54 to remove the autodrop potential from line 56.

At this point, the forward reaction commences and continues until completion (e.g. some 20 seconds). At the end of the forward reaction time, microprocessor 50 causes signal voltage module 54 to apply a measurement potential to cell 10 to commence the reverse reaction. Again, there is an initial surge of current which is ignored by the measurement circuitry. At the end of the surge time (e.g., t0), an initial current measurement is taken, followed by subsequent measurements at subsequent intervals (e.g. t1, t2, t3 ... ). As will be hereinafter understood, microprocessor 50 selects one of the current measurements and calculates the glucose concentration based upon the linear relationship which has been precalibrated using the constants provided by ROM 68. Additionally, microprocessor 50 accumulates all of the current measurement values; and integrates them over the measurement time to obtain a value for the total charge transferred during the reverse reaction. This value is converted to concentration to provide a comparative value to the single measurement value. Additionally, microprocessor 50, in combination with the other modules in the system, carries out a series of tests to determine that the signals being detected by signal detector 60 are following the Cottrell current relationship.

Figure 5:
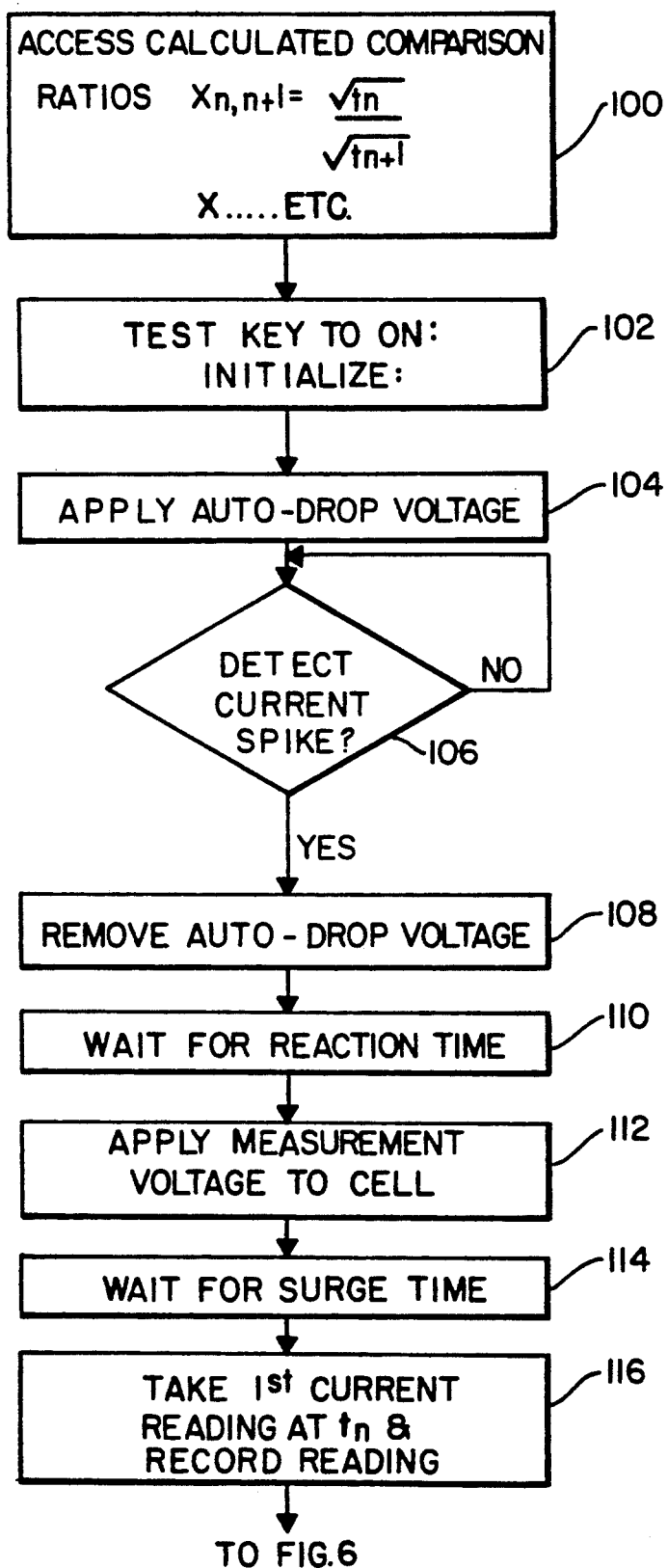

These procedures are described in FIGS. 5 and 6. Initially, each of the precalculated comparison ratios ($x_{1,2}$, $x_{2,3}$ etc.) is accessed (box 100) and stored. Thus, for each of a plurality of measurement times $t_n$, $t_{n+1}$, a comparison ratio $x_{n,\,n+1}$ is accessed and stored. Next, the user inserts the test cell and depresses the test key. The system's circuits are then initialized (box 102) and the autodrop voltage is applied to cell 10 (box 104). Signal detector 60 then awaits a current spike indicating that a blood sample has been placed in well 20 (box 106). If no current spike is detected, the program simply recycles until the current spike is sensed (box 106). At this point, the autodrop voltage is removed (box 108), and the system waits until the reaction time expires (box 110). Then, a measurement voltage is applied to cell 10 from signal voltage module 54, and a first current reading is taken at t0 and recorded (box 116). Next, (in FIG. 6) a subsequent current reading is taken (e.g. t1) and recorded (box 118).

At this point, the current value measured at $t_n$ and $t_{n+1}$ are accessed and the ratio thereof is derived. That ratio is then compared to the prestored comparison constant $x_{n,\,n+1}$. If the ratios are not "similar", then it is known that the measured values of current are not following a predetermined Cottrell current relationship. By the term "similar" is meant that the calculated current ratio does not differ from the precalculated comparison constant x by more than a predetermined error value (box 120).

In the event the comparison "fails", an error condition is reported (box 122). If the comparison succeeds, the process continues with microprocessor 50 integrating the current values taken at $t_n$ and $t_{n+1}$ over the time period $(t_{n+1})-(t_n)$, and accumulating the value, (it being remembered that the integration of current over time gives a value of charge transfer during that time, see box 126). At some time during the measurement cycle, a sample measurement time is designated. At such time, the current reading taken at that time (box 127) is subsequently converted to a "sample" glucose concentration value (box 134).

A determination is then made as to whether the system has arrived at the last time value in the measurement cycle (box 128). If not, the system recycles back to box 118 after incrementing n (box 124) and takes the next current reading at the next time. The ratio of $i_{tn}$ to $i_{tn+1}$ is then calculated and compared to the prestored comparison constant, etc. It should be understood that the comparison constants need not be calculated for just those current ratios taken at succeeding measurement times, but may be calculated for various diverse measurement times.

When it has been determined that the last current value has been measured (box 128), the system computes the integral glucose concentration (box 130) and the sampled glucose concentration (134). The system then compares the calculated integrated and sampled glucose concentrations (box 136) and determines whether they are similar or not (box 138) with the results being as shown in boxes 140 or 142.

From the above it can be seen that, in addition to taking a single sample measurement, an integrated sample measurement is derived to enable a comparison to be made to assure that the reading can be relied upon. Furthermore, the comparison of the current ratios with the predetermined comparison constants enables the system to precisely determine that the measured current values have followed an expected Cottrell current relationship. Thus, if there is an aberration in the test system or in the cell, erroneous readings are avoided.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A biosensor system for determining whether a current through a reaction zone is varying in accordance with a predetermined Cottrell current relationship, the combination comprising:

a test cell including electrode means and a reaction zone with analyte reactant;

means for obtaining a plurality of readings of current in said reaction zone over a plurality of measurement times, after a sample containing an analyte is placed in said reaction zone;

means for storing at least a comparison constant for a pair of succeeding measurement times, said comparison constant evidencing the inverse ratio of the square root of a measurement time divided by the square root of a subsequent measurement time;

means for deriving a ratio of the current readings obtained at said pair of succeeding measurement times; and means for comparing said ratio of said current readings and said comparison constant for said pair of succeeding measurement times to determine if they are similar and if not, reporting an error condition.

2. The system as defined in claim 1 wherein: said storing means includes a plurality of comparison constants for a plurality of succeeding measurement times; and said deriving means derives ratios of current readings taken at said succeeding measurement times, and said comparison means compares said ratios with corresponding comparison constants, whereby said system determines if said current readings are following said Cottrell current relationship.

3. The system as defined in claim 2 wherein said test cell includes two electrodes which extend into a reaction zone, said electrodes covered by an analyte reactant containing layer.

4. In a system for measuring a current i passing through a reaction zone of a test cell, which current, in dependence upon the concentration of an analyte in the reaction zone, changes to follow one of a family of curves whose shape is defined by the Cottrell equation, a method for determining that said current is changing in accordance with the Cottrell equation, comprising the steps of:

(a) measuring said current i at a plurality of measurement times $t_n$, $t_{n+1}$, $t_{n+2}$ . . . to derive current values $i_n$, $i_{n+1}$, $i_{n+2}$ . . . ;

(b) calculating at least the value of the ratio of $$\frac{\sqrt{i_{n+1}}}{\sqrt{i_n}}$$

to obtain a comparison constant;

(c) calculating the value of the ratio of $$\frac{i_n}{i_{n+1}} ;$$

(d) comparing the comparison constant calculated in step b and with the ratio calculated in step c; and (e) if said comparison indicates a dissimilarity, providing a signal indicating that said measured current in said test cell is not changing in accordance with said Cottrell equation.

5. The method as defined in claim 4 wherein the ratio defined in step b is calculated for a plurality measurement times to obtain a plurality of comparison constants.

6. The method as defined in claim 5 wherein a ratio, as defined in step c, is calculated for currents measured at each of the measurement times which are used to derive the comparison constants of claim 5.

7. The method of claim 6 wherein step d compares the comparison constants with ratios derived in step c for corresponding measurement times and step e provides a signal if any of said comparisons indicate a dissimilarity.

8. The method of claim 7 wherein said comparison constants obtained by step b are precalculated and stored.

* * * * *